United States Patent
Van Antwerp et al.

(10) Patent No.: US 6,443,942 B2
(45) Date of Patent: Sep. 3, 2002

(54) MEDICATION DEVICE WITH PROTEIN STABILIZING SURFACE COATING

(75) Inventors: William Peter Van Antwerp, Valencia; Poonam S. Gulati, La Canada; Gerald E. Adomian, Los Angeles, all of CA (US)

(73) Assignee: MiniMed, Inc., Northridge, CA (US)

( * ) Notice: Subject to any disclaimer, the term of this patent is extended or adjusted under 35 U.S.C. 154(b) by 0 days.

(21) Appl. No.: 09/876,569

(22) Filed: Jun. 6, 2001

Related U.S. Application Data

(63) Continuation-in-part of application No. 09/042,138, filed on Mar. 13, 1998, now abandoned, which is a continuation of application No. 08/742,377, filed on Nov. 1, 1996, now abandoned, and a continuation-in-part of application No. 09/324,783, filed on Jun. 3, 1999, now abandoned.

(51) Int. Cl.[7] .................. A61L 33/00; A61L 17/00; A61L 2/02
(52) U.S. Cl. .................. 604/890.1; 604/891.1; 604/892.1; 604/67; 604/70; 604/131; 604/151; 623/1; 623/2; 623/6; 427/2.1; 427/2.24; 427/2.25; 427/2.28; 427/2.3; 427/508; 427/407.1; 427/409
(58) Field of Search .................. 427/2.24, 2.1, 427/2.25, 2.28, 2.3, 508, 402.1, 409; 604/890.1, 891.1, 892.1, 67, 70, 131, 151; 623/1, 26

(56) References Cited

U.S. PATENT DOCUMENTS

| | | |
|---|---|---|
| 2,402,950 A | 7/1946 | Culver et al. |
| 2,519,541 A | 8/1950 | Bryant |
| 4,034,959 A | 7/1977 | Morrison |
| 4,163,544 A | 8/1979 | Fowler et al. |
| 4,373,009 A | 2/1983 | Winn |
| 4,373,527 A | 2/1983 | Fischell |
| 4,560,375 A | 12/1985 | Schulte et al. |
| 4,568,250 A | 2/1986 | Falk et al. |
| 4,569,641 A | 2/1986 | Falk et al. |
| 4,573,994 A | 3/1986 | Fischell et al. |
| 4,626,244 A | 12/1986 | Reinicke |
| 4,636,150 A | 1/1987 | Falk et al. |
| 4,654,006 A | 3/1987 | Kusano et al. |
| 4,714,234 A | 12/1987 | Falk et al. |
| 4,769,013 A | 9/1988 | Lorenz et al. |
| 4,783,441 A | * 11/1988 | Thurow .................. 424/94.3 |
| 4,950,256 A | 8/1990 | Luther et al. |
| 4,958,661 A | 9/1990 | Holtermann et al. |
| 5,001,009 A | 3/1991 | Whitbourne |
| 5,019,260 A | 5/1991 | Gsell et al. |
| 5,069,989 A | 12/1991 | Whitbourne et al. |

(List continued on next page.)

FOREIGN PATENT DOCUMENTS

| EP | 0 747 069 A2 | 12/1996 |
|---|---|---|
| EP | 0 826 382 A2 | 3/1998 |

(List continued on next page.)

OTHER PUBLICATIONS

Thurow, H and Geisen, K, Stabilisation of dissolved proteins against denaturation at hydrophobic interfaces, Diabetologia, Springer–Verlag, 1984.*

Primary Examiner—Shrive P. Beck
Assistant Examiner—Jennifer Kolb Michener
(74) Attorney, Agent, or Firm—Gates & Cooper LLP

(57) ABSTRACT

The present invention provides medical devices such as medication infusion pumps having internal surfaces that are treated to inhibit protein denaturation. In accordance with the invention, hydrophilic internal surfaces and related coating methods are provided to reduce or eliminate accumulation of medication deposits which can otherwise occur when handling complex protein-based medications. Preferred hydrophilic pump surfaces include hydrophilic surfactants (PEO) or (PEG) coatings which exhibit very low protein adsorption characteristics. Several methods are disclosed for producing such treated surfaces including the covalent attachment of hydrophilic surfactants.

20 Claims, 1 Drawing Sheet

U.S. PATENT DOCUMENTS

| | | |
|---|---|---|
| 5,077,210 A | 12/1991 | Eigler et al. |
| 5,128,170 A | 7/1992 | Matsuda et al. |
| 5,178,366 A | 1/1993 | Kojima et al. |
| 5,183,472 A | 2/1993 | Jaehrling et al. |
| 5,229,172 A | 7/1993 | Cahalan et al. |
| 5,328,954 A | 7/1994 | Sarangapani |
| 5,330,911 A | 7/1994 | Hubbell et al. |
| 5,331,027 A | 7/1994 | Whitbourne |
| 5,415,938 A | 5/1995 | Cahalan et al. |
| 5,433,710 A | 7/1995 | Van Antwerp et al. |
| 5,607,475 A | 3/1997 | Cahalan et al. |
| 5,609,629 A | 3/1997 | Fearnot et al. |
| 5,620,738 A | 4/1997 | Fan et al. |
| 5,643,681 A | 7/1997 | Voorhees et al. |
| 5,648,442 A | 7/1997 | Bowers et al. |
| 5,662,960 A * | 9/1997 | Hostettler et al. ......... 427/2.28 |
| 5,672,638 A | 9/1997 | Verhoeven et al. |
| 5,702,754 A | 12/1997 | Zhong |
| 5,702,818 A | 12/1997 | Cahalan et al. |
| 5,711,959 A | 1/1998 | Kohler et al. |
| 5,939,208 A | 8/1999 | Stoy |
| 6,013,855 A | 1/2000 | McPherson et al. |

FOREIGN PATENT DOCUMENTS

| | | | |
|---|---|---|---|
| WO | WO 98/07458 | 2/1998 | |
| WO | WO 98/08553 | 3/1998 | |
| WO | WO 98/10805 | 3/1998 | |
| WO | WO 98/19627 | * 5/1998 | ............ A61F/2/00 |

* cited by examiner

MEDICATION DEVICE WITH PROTEIN STABILIZING SURFACE COATING

CROSS REFERENCE TO RELATED APPLICATIONS

This application is a Continuation-in-part Application claiming priority under Section 120 to U.S. patent application Ser. No. 09/042,138, filed Mar. 13, 1998, now abandoned, which is a continuation application of U.S. patent application Ser. No. 08/742,377 filed Nov. 1, 1996, now abandoned; and is a Continuation-in-part Application claiming priority under Section 120 to U.S. patent application Ser. No. 09/324,783, filed Jun. 3, 1999, now abandoned the contents of each of which are incorporated herein by reference.

FIELD OF THE INVENTION

This invention relates generally to reusable and disposable medical devices that are used to store, contain or deliver protein-based medications. More particularly, this invention relates to improved medical devices that have one or more protein-contacting surfaces treated to reduce the protein adsorption and denaturation that can occur on an untreated surface.

BACKGROUND OF THE INVENTION

Medication infusion pumps are generally known in the art for use in delivering a selected medication to a patient in a preprogrammed or patient-programmed manner. In recent years, infusion pumps have been developed in compact form and adapted to deliver a specific medication, such as insulin, to the patient in patient-programmed continuous doses over an extended time period. Medication infusion pumps have also been used to deliver a wide variety of other drugs to a patient. Such medications or drugs include, for example, baclofen, morphine and other pain medications, various antibiotics, and a number of chemotherapeutic agents.

As protein-based medications become more prevalent, problems arise in reliable long-term administration of these medications to a patient. More specifically, bolus drug injections are not optimal to achieve relatively constant blood concentration levels. Many of the newer protein-based medications are relatively complex, having a high molecular weight, such that bolus therapy subcutaneous drug delivery can be problematic due to relatively fast clearance by the renal and hepatic systems.

One problem encountered with medical devices is that medication contacting surfaces are typically constructed from materials, such as metals, polymers or other materials, that have low free surface energies, typically on the order of about 40 dyne/cm2. At this low free surface energy, protein-based medications can be adsorbed quite readily and can subsequently denature on the medication contacting surfaces. Once denaturation occurs, the protein-based substances can aggregate to a form that is generally not bioavailable to the patient and may in some cases lead to undesired immunological response.

While practitioners in the art have employed a variety of methods to address problems associated with the denaturation of proteins at surfaces in medical devices, protein adsorbtion continues to be a problem in the field. For example, over time coating materials may disadhere from a matrix, thereby exposing proteins to the destabilizing surfaces. In addition, because proteins are heterogeneous in both their structural and chemical properties, it is difficult to identify a single coating material that works to inhibit the denaturation of the spectrum of different protein-based medications used in medical devices. Consequently there is a need in the art to identify additional coatings and methods for attaching them to a surface of a medical device, in particular those tailored to inhibit the denaturation of specific protein-based medications.

The present invention meets this need in the art by providing methods for generating improved medical devices having a hydrophilic internal surface coatings that are highly stable in the presence of complex protein-based medications, in particular, insulin based medications.

SUMMARY OF THE PREFERRED EMBODIMENTS

The present invention provides methods for inhibiting the denaturation of proteins such as insulin at surfaces in medical devices. In particular, the invention provided herein identifies specific polymers that retain the ability to inhibit the destabilization and/or degradation of insulin even after undergoing the chemical modification required to permanently attach the polymers to a surface in a medical device. In accordance with one aspect of the present invention, there is provided a medical device having a surface contacted by a selected protein-based medication. Typically the surface has a covalently attached surface treatment that defines a surface contact angle less than about 45 degrees, and also exhibits a protein adsorption profile of less than about 1.0 microgram per square centimeter when measured with insulin.

In more specific embodiments, the medical device is a medication infusion pump. The medication infusion pump can be reusable or disposable, and can be externally worn or implantable. The medical device according to the invention is not limited to a medication infusion pump, however, but can also be a device such as a prefilled medication cartridge, a syringe, a catheter, an IV bag, and the like.

In one preferred embodiment the surface is a metallic surface such as titanium. In another preferred embodiment, the surface is a non-metallic polymeric surface, such as a rubber, a polyurethane, a polyethylene, a polypropylene or a polyvinylchloride. In a particular preferred embodiment, the polymeric surface is comprised of a bromobutyl rubber or a chlorobutyl rubber.

Preferably, the surface treatment is a coating comprised of polymeric materials such as hydrophilic polyurethanes, polyureas, acrylics, polycarbonates or other hydrophilic materials, in particular materials such as polyethylene glycols, polyethylene/polypropylene glycol copolymers or other poloxamers which are chemically (covalently) attached to the treated surface.

A preferred illustrative embodiment of the invention consists of a medical device having a surface comprising a polypropylene glycol/polyethylene glycol polymer covalently attached thereto, wherein the polypropylene glycol/polyethylene glycol polymer has a molecular weight of about 1800 Daltons and comprises a compound of the following general formula:

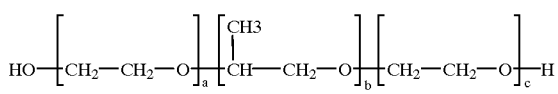

Typically, the surface having the polypropylene glycol/polyethylene glycol polymer covalently attached thereto defines a surface contact angle less than about 45 degrees and exhibits an insulin adsorption profile of less than about 1.0 microgram per square centimeter. In preferred embodiments, the surface contact angle is less than about 35 degrees and the surface exhibits an insulin adsorption profile of less than about 0.5 microgram per square centimeter. In highly preferred embodiments, the surface exhibits an insulin adsorption profile of less than about 0.1 microgram per square centimeter.

In accordance with a further aspect of the present invention, there is provided a medication infusion device for contacting a selected protein-based medication, the device having a surface for contacting the medication. The surface has a coating to reduce the surface contact angle and protein adsorption profile. Preferably, the surface is a polymeric surface as set forth above, and the coating is a polymeric material as set forth above.

In accordance with still another aspect of the present invention, a component for use in a medication infusion device as described herein is provided. The component has a surface having a covalently attached surface treatment that defines a surface contact angle less than about 45 degrees and exhibits a protein adsorption profile of less than about 1.0 microgram per square centimeter when measured with insulin.

In accordance with yet another aspect of the present invention, there is provided a method of treating a surface for use in a medical device for contacting a selected protein-based medication. The method includes the step of treating the surface to produce a covalently attached surface treatment that defines a surface contact angle less than about 45 degrees and exhibits a protein adsorption profile of less than about 1.0 microgram per centimeter when measured with insulin.

Preferably the surface is a polymeric surface as set forth above, and the treating step includes the application of a coating of a polymeric material as set forth above to the polymeric surface.

In a more specific embodiment, the polymeric material is applied to the surface by dipping, spraying, pre-polymerization followed by polymeric attachment, RF-plasma attachment, grafting, or silane-based primer attachment, and subsequently cured, preferably by exposure to actinic radiation (e.g., UV radiation), free radicals, elevated temperature, RF energy, or by other chemical reactions. If needed, the application and curing steps are repeated to ensure that the entire surface is provided with the coating.

Components for medical devices treated according to the inventive method, and medical devices including such components, ate also provided.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

Figure 1:
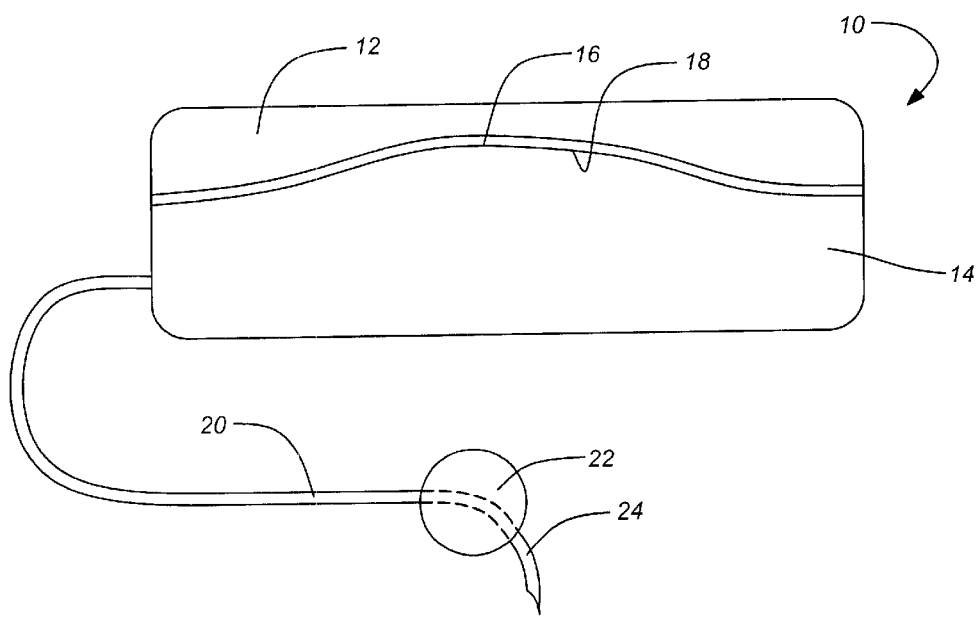
FIG. 1 is side sectional view depicting a typical externally mountable infusion device.

The invention disclosed herein provides medication storage and delivery devices having one or more internal surfaces bearing a hydrophilic coating which substantially reduces or eliminates accumulation of undesired medication deposits particularly when the medication device is used to deliver complex protein based medications such as insulin. The hydrophilic internal surfaces have been found to significantly reduce and/or eliminate undesired adsorption of insulin proteins on internal pump surfaces.

The invention can be applied to a wide range of different types of devices such as infusion pumps, including both reusable and non-reusable pumps, as well as to both implantable and externally worn pumps. For example, the invention is applicable to an externally worn, gas powered infusion device as described in U.S. Pat. No. 5,785,688; an implantable constant-flow medication infusion pump as described in U.S. patent application Ser. No. 08/871,830; and the pumps described in U.S. patent application Ser. No. 09/253,382 and Ser. No. 09/253,383 the disclosures of which are incorporated herein in their entireties by reference, as well as other medical devices that employ flexible displaceable membranes. These exemplary medical devices, which can be beneficially treated according to the present invention, include flexible metallic and non-metallic internal membranes which separate medicament reservoirs from propellant reservoirs. Such pumps can be driven by an elastomeric sponge surrounding the medicament reservoir (e.g., from Science Incorporated); in which a propellant reservoir is prefilled with a gas or chemical solution to generate a gas (e.g., from River Medical); or in which a gas is generated electrochemically within the propellant reservoir (e.g., from Elan Corporation or CeramTec, Inc.).

The invention can further be applied to a variety of pump surfaces including both metallic and non-metallic surfaces to reduce the surface contact angle for hydrophilic characteristics. Furthermore, the invention is not limited to pumps, but is also suitable for application to any medical device having one or more components that are contacted by a selected protein-based medication. Such devices include, without limitation, prefilled medication cartridges having internal pistons; polymeric syringe bodies, reservoirs, plungers and plunger O-rings; polymeric catheters; IV bags; polymeric bottles and other storage containers; or the like.

Additional exemplary medical devices include replaceable or disposable syringes or reservoirs for medication infusion pumps, such as those commercially available from MiniMed Inc. and Disetronic. For a detailed description of the overall construction and operation of implantable infusion pumps that are beneficially treated according to the present invention, see U.S. Pat. Nos. 4,373,527 and 4,573,994, both of which are incorporated by reference herein. For a detailed description of the construction and operation of a miniature pump mechanism, see U.S. Pat. Nos. 4,568,520; 4,569,241; 4,636,150; and 4,714,234, each of which are incorporated by reference herein.

The adsorption and subsequent denaturation of the protein-based medication on a surface is functionally related to its surface free energy. Accordingly, the present invention relates to a medication device wherein one or more internal surfaces are coated to achieve a significant reduction in surface free energy such that the ability of such surfaces to destabilize proteins such as insulin is reduced. A variety of insulin proteins that are stabilized by such surface treatments are well-known in the art, including human and porcine or bovine insulin as well as to fast acting analogs of insulin (typically human insulin), which include: human insulin, wherein Pro at position B28 is substituted with Asp, Lys, Leu, Val, or Ala, and wherein position B29 is Lys or is substituted with Pro; AlaB26-human insulin, des(B28–B30) human insulin; and des(B27) human insulin. Illustrative insulin proteins are disclosed in U.S. Pat. No. 5,514,646, WO 99/64598, WO 99/6459A2 and WO 96/10417A1.

Turning now to FIG. 1, an externally worn medication infusion pump 10 includes propellant reservoir 12 and medicament reservoir 14 separated by flexible non-metallic (e.g., polymeric) membrane 16. Membrane 16 has a surface 18 in contact with the medicament in reservoir 14. Surface 18 is provided with a surface treatment according to the present invention. Preferably, the propellant reservoir 12 contains a gas generated electrochemically or chemically to apply pressure to the membrane 16 in order to expel the medicament from the medicament reservoir 14. The medicament is delivered to the patient via catheter 20 and an infusion set 22 having cannula 24.

Figure 2:
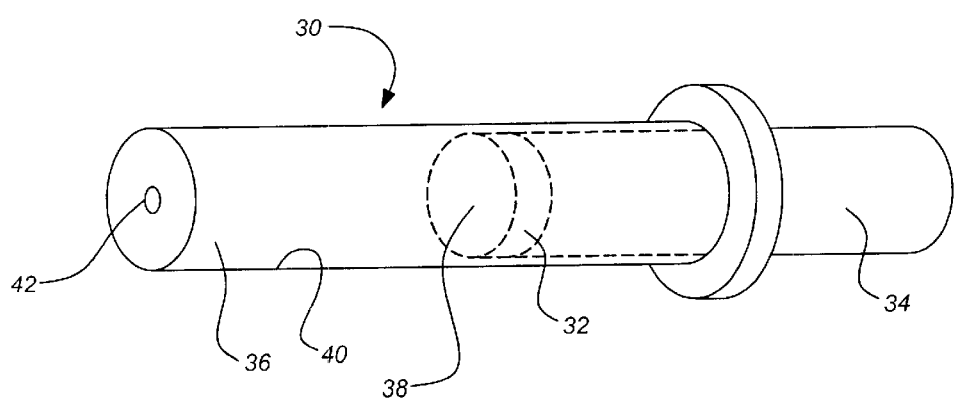
FIG. 2 is a side sectional perspective view, partially in phantom, of a medicament reservoir used with an infusion device.

In FIG. 2, a prefilled medicament cartridge 30 for use with a medicament infusion pump includes a non-metallic piston 32 driven by plunger 34 into reservoir 36. Piston 32 has a surface 38 which is treated according to the invention. Reservoir 36, which can be formed from a non-metallic material such as glass, a polymer or the like, has a surface 40 which also can be treated according to the invention. As piston 32 is urged inward into reservoir 36, the medicament within reservoir 36 is supplied via orifice 42 into the medicament infusion pump (not shown) in which cartridge 30 has been inserted.

Medical devices having surfaces comprised of both metallic and non-metallic materials, and components of such medical devices which are comprised of both metallic and non-metallic materials, are beneficially prepared according to the present invention. The metallic surfaces can be comprised of, for example, titanium. The non-metallic surfaces can be comprised, for example, of a polymeric material, for example a rubber such as bromobutyl rubber or chlorobutyl rubber, a polyurethane, a polyethylene, a polypropylene, a polyvinylchloride, or other similar polymeric materials. The medical device components can be made of a polymeric material, such as those listed above, or can be formed from a polymer laminate (e.g., two or more layers of different polymeric materials) or a metallized polymeric material, in which case the polymeric material has a nonmetallized surface which has a surface treatment according to the invention.

The surface treatment according to the invention can be, for example, a coating formed from a polymeric material. Specific polymeric materials useful to provide a surface treatment according to the invention include, without limitation, materials such as hydrophilic polyurethanes, polyureas, acrylics, as well as other hydrophilic components. Particular materials include polyethylene glycols, polyethylene/polypropylene glycol copolymers and other poloxamers. These coatings preferably are covalently bonded to the surface which is being treated.

One particular method for forming the coating includes the steps of adsorbing the polymeric material to the surface, and then covalendy attaching the polymeric material to the surface by exposure to UV radiation, RF energy, heat, X-ray radiation, gamma radiation, electron beams, or the like. If needed, the foregoing application and curing steps ate carried out at least twice, more particularly at least three times, in order to avoid bubble formation and provide uniform surface coverage.

Another particular method includes the step of covalently attaching a linker molecule to the surface. Linker molecules that are useful in this embodiment of the inventive method include, without limitation, silanes of the formula SiX3-R, wherein X is a methyl group or a halogen atom such as chlorine and R is a functional group which can be a coating material as described herein or a group which is reactive with a coating material. Particular silane-terminated compounds include vinyl silanes, silane-terminated acrylics, silane-terminated polyethylene glycols (PEGs), silane-terminated isocyanates and silane-terminated alcohols. The silanes can be reacted with the surface by various means known to those skilled in the art. For example, dichloro methyl vinyl silane can be reacted with the surface in aqueous ethanol. The linker molecule strongly binds to the surface via —O—Si bonds or directly with the silicon atom. The vinyl group of the silane can then be reacted with polymeric materials as described herein using appropriate conventional chemistries. For example, a methacrylate-terminated PEG can be reacted with the vinyl group of the silane, resulting in a PEG that is covalently bonded to the surface of the medication device.

In accordance with a preferred surface treatment and method, a hydrophilic surfactant is applied to the selected surface of the medical device to significantly reduce adsorption of a protein-based medication such as insulin. Several hydtophilic surfactants are available for this purpose, including Genapol™, a block ethylene/propylene copolymer having a molecular weight of about 1800 Daltons, available from Hoechst Celanese Co. of Somerville, N.J. Other hydrophilic surfactants include Tween, a polyoxyethylene sorbitan available from Sigma Biochemicals of St. Louis, Mo., and Brij, a polyoxyethylene ether also available from Sigma Biochemicals of St. Louis, Mo.

Due to the highly heterogeneous structural and chemical characteristic of different proteins, those skilled in the art assess the compatibility between a specific protein such as insulin and the hydrophilic surfactant that is applied to the selected surface of the medical device to reduce adsorption of a protein-based medication (e.g. Genapol™). In this context, artisans understand that proteins are amphiphilic substances which have very different characteristics that influence their interaction with other molecules such as hydrophilic surfactants known in the art. Specifically, different sequences of the various amino acids in the primary sequence of a polypeptide condition the formation of the hydrophilic and hydrophobic regions within the protein and the repulsive and attractive forces between these regions are balanced to form the complex three dimensional structure of the protein's native state. As it is not possible to predict exactly how a specific protein and hydrophilic polymer will interact, each hydrophilic surfactants that could be used to coat surfaces of medical devices is assessed to determine whether it has a structure that promotes the maintenance of that protein's unique native state (i.e. the non-denatured state). As disclosed herein, hydrophilic surfactants including a polyethylene glycol (PEG) moiety as their hydrophilic segment, in particular a polypropylene glycol/polyethylene glycol polymer having a molecular weight of about 1800 Daltons and comprising a compound of the general formula disclosed herein (e.g. Genapol PF-10™, available from Hoechst Celanese Co. of Somerville, N.J.) are highly compatible with insulin polypeptides and promote the maintenance of this specific protein's native state. Most importantly, these hydrophilic surfactants function to preserve the complex three dimensional structure of insulin even when they are covalently attached to a substrate known to denature this protein.

Covalent modifications to hydrophilic polymers such as Genapol™ involve the generation reactive polymer sites which then covalently attach the polymer to a surface (for example in a medical device), a process which alters the complex 3D architecture of the polymer. Because this process alters the architecture of polymers, such modifications can correspondingly effect their protein stabilizing properties. Consequently, it is not possible to predict exactly how such covalent modifications will effect each hydrophilic polymer's ability to promote the stability of a specific protein and whether the stabilizing property of a given polymer will be compromised by such modifications. This unpredictability is illustrated for example, by reports that small changes to the side chain structures of various polymers (or even alterations to their molecular weights) impact their ability to stabilize proteins (see, e.g., Thurow et al., Diabetologia (1984) 27: 212–218).

The observation that polymers such as Genapol PF-10™ retain desirable properties even after being chemically modified and covalently affixed to a matrix is surprising in view of reports that teach that even slight alterations to these polymers can dramatically effect their ability to stabilize proteins. Moreover, it is believed that the active principle of polypropylene glycol polymers involves how the alternating arrangement of hydrophobic lateral methyl groups and hydrophilic oxygen bridges in the polymer contact a hydrophobic interface. Consequently it is surprising that covalent modifications to such polymers which have the potential to disturb this arrangement do not in fact compromise the polymer's ability to promote the stability of a protein. As disclosed herein however, certain polymers such as the polypropylene glycol/polyethylene glycol polymer described below can be covalently modified in this manner and still generate an improved surface, i.e. one that defines a surface contact angle less than about 45 degrees and exhibits an insulin adsorption profile of less than about 1.0 microgram per square centimeter.

The invention disclosed herein has a number of representative embodiments. A preferred illustrative embodiment of the invention consists of a medical device having a surface comprising a polypropylene glycol/polyethylene glycol polymer covalently attached thereto, wherein the polypropylene glycol/polyethylene glycol polymer has a molecular weight of about 1800 Daltons and comprises a compound of the following general formula:

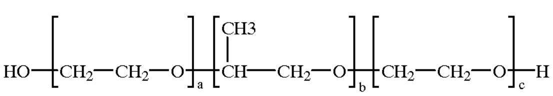

(see, e.g., Thurow et al., Diabetologia (1984) 27: 212–218). Preferred unbranched polypropylene glycol/polyethylene glycol polymers typically have a mean number of about 30.1 polypropylene glycol chain links (subunit "b" above) and about 2.2 polyethylene glycol chain links (subunit "a" above). Typically, the surface having the polypropylene glycol/polyethylene glycol polymer covalently attached thereto defines a surface contact angle less than about 45 degrees and exhibits an insulin adsorption profile of less than about 1.0 microgram per square centimeter. In preferred embodiments, the surface contact angle is less than about 35 degrees and the surface exhibits an insulin adsorption profile of less than about 0.5 microgram per square centimeter. In highly preferred embodiments, the surface exhibits an insulin adsorption profile of less than about 0.1 microgram per square centimeter.

A related embodiment of the invention is a method of inhibiting the destabilization and/or denaturation of insulin on a surface comprising covalently attaching to the surface a polypropylene glycol/polyethylene glycol polymer comprising the following general formula:

wherein the polypropylene glycol/polyethylene glycol polymer has a molecular weight of about 1800, and wherein the treatment produces a surface that defines a surface contact angle less than about 45 degrees and exhibits an insulin adsorption profile of less than about 1.0 microgram per square centimeter. In preferred embodiments, the surface contact angle is less than about 35 degrees and the surface exhibits an insulin adsorption profile of less than about 0.5 microgram per square centimeter. In highly preferred embodiments, the surface exhibits an insulin adsorption profile of less than about 0.1 microgram per square centimeter.

Yet another embodiment of the invention is a process for treating a surface to inhibit the denaturation of insulin on the surface comprising covalently attaching to the surface a polypropylene glycol/polyethylene glycol polymer comprising the following general formula:

wherein the polypropylene glycol/polyethylene glycol polymer has a molecular weight of about 1800, and wherein the process produces a surface that defines a surface contact angle less than about 45 degrees and exhibits an insulin adsorption profile of less than about 1.0 microgram per square centimeter. A closely related embodiment consists of a surface treated according to this process.

The methods and treated surfaces disclosed herein can be applied to a wide variety of medical devices such as infusion pumps, medication cartridges, syringes, catheters and IV bags etc. In one embodiment, the medical device is externally worn. In another embodiment, the medical device is implantable. As disclosed herein the a wide variety of surfaces present in medical devices that come into contact with protein based medications can be modified via the covalent attachment of polypropylene glycol/polyethylene glycol polymers. In one embodiment, the surface is metallic such as a titanium surface. Alternatively, the surface is non-metallic and comprised of a material typically used in medical devices such as rubber, polyurethane, polyethylene, polypropylene or polyvinylchloride etc.

The polypropylene glycol/polyethylene glycol polymers can be attached to a selected surface by any one of a wide variety of methods known in the art. Typically, the polymer is covalently attached to the surface by a method selected from the group consisting of polymeric attachment, RF-plasma attachment, grafting, or silane-based primer attachment. The invention disclosed herein has advantages over previously described coating methods because the polypropylene glycol/polyethylene glycol polymers can be securely affixed to a surface via covalent attachment. In addition, as noted above, a significant and surprising finding is that these polymers continue to inhibit the denaturation of insulin even when their chemical structure is modified as part of the covalent attachment process.

As one example of the invention, a 1.0% solution of Genapol™ is prepared in isoptopanol and then contacted with the selected surface, such as a metal or elastomeric surface of a medication device (or reservoir) by filling the medication device (or reservoir) with the Genapol™ solution. The Genapol™ surfactant which is non-ionic in nature binds to the surface, and the isopropanol solvent can be readily removed under mild conditions of heat and vacuum. After this drying step, the treated surface is placed in a radio frequency (RF) chamber in the presence of oxygen, argon, or both, and 100–200 watts of RF power are applied to result in covalent attachment of the polymer to the surface. If required, this process is repeated at least once. An exemplary RF chamber is available from Technics, Inc. of Newark, N.J. During the RF treatment step, the oxygen and/or argon plasma generates significant ultraviolet light which creates reactive polymer sites which then covalently attach to the surface. In the illustrative example, each RF step proceeded for about 10 minutes using an RF frequency of about 100 kHz.

After this surface treatment with the Genapol™ surfactant and plasma, as described above, the surface contact angle is less than 10 degrees as measured by direct contact angle measurement. In this regard, the contact angle of water is a measure of its hydrophilic characteristics. A low contact angle means that the surface is wetted, whereas a high contact angle means that the surface is non-wetted or hydrophobic. For instance, the contact angle of an untreated or uncoated polymeric surface ranges from about 88 to 125 degrees.

Protein adsorption is significantly reduced as a result of the inventive surface treatment, typically to about 1.0 microgram or less per square centimeter of the treated surface, more specifically when measured with insulin. For example, insulin adsorption after the foregoing Genapol™ surface treatment is less than 0.1 microgram per square cm of the surface, as compared to an adsorption of about 1.5 microgram per square cm for the uncoated surface. Similar surface treatments using other hydrophilic surfactants such as those identified above yield results of similar magnitude, although Genapol™ is believed to provide the best reduction in insulin adsorption.

A further alternative coating method in accordance with the invention utilizes a hydrophilic polyurethane, such as that marketed by Thermedics, Inc. of Woburn, Mass., under the name Biomer. In this method, Biomer is prepared in an approximate 7.0% solution with tetrahydrofuran (THF) and the surface to be coated is dipped therein. The dip coated surface is subsequently dried for about six hours at about 45 degrees Celsius. Subsequent hydration as by exposure to water for about one hour results in a surface contact angle and insulin adsorption profile that is too low to measure, i.e., less than about 0.04 micrograms per square centimeter.

A hydrophilic surface coating can also be prepared by the use of bovine serum albumin (BSA) dissolved in a phosphate buffered saline (PBS) solution with a concentration of about 5 milligrams per milliliter. The medication device surface to be coated is dipped into this solution and allowed to dry. After drying, the coated surface is dipped a second time into the BSA solution and then immediately dipped into a solution of glutaraldehyde in deionized water with a concentration of about 2.5% which functions to cross link the protein both to the surface and also to itself. After drying for about two hours, at about 37 degrees Celsius, the resultant surface contact angle is about 30 degrees, and it is believed that a comparable reduction in insulin adsorption will result.

There are several ways to covalently attach a hydrophilic coating to the surface of the medication device. These include radiation, electron beam and photo induced grafting, polymerization chemical grafting and plasma deposition of polymers. In general, these methods involve an energy source and a monomer of the desired hydrophilic polymer. For example, acrylonitrile can be grafted onto a surface by irradiation of acrylonitrile vapor in contact with the surface. The resulting polymer, polyacrylonitrile (PAN) has excellent hydrophilic properties with very minimal protein interaction with the surface. A wide variety of polymers can be produced in this manner, the only requirement being that the monomer be available in reasonable purity with enough vapor pressure to be reactive in the deposition system.

Accordingly, the present invention provides a treated surface exhibiting significant hydrophilic properties, with a reduced surface contact angle, preferably of less than about 45 degrees, and more preferably less than about 35 degrees. This treated surface has a low free energy and has provided demonstrated protein stability.

A variety of modifications and improvements to the present invention will be apparent to those skilled in the art. For example, it will be apparent that the invention can be applied to a broad scope of medical devices having a surface wherein avoidance of protein-based deposits is desired. While the description above refers to particular embodiments of the present invention, it will be understood that many modifications may be made without departing from the spirit thereof. The accompanying claims are intended to cover such modifications as would fall within the true scope and spirit of the present invention.

The presently disclosed embodiments are therefore to be considered in all respects as illustrative and not restrictive, the scope of the invention being indicated by the appended claims, rather than the foregoing description, and all changes which come within the meaning and range of equivalency of the claims are therefore intended to be embraced therein. All patent and patent application and literature references cited in the present specification are hereby incorporated by reference in their entirety.

What is claimed is:

1. A medical device comprising a surface having a polypropylene glycol/polyethylene glycol polymer covalently attached thereto, wherein the polypropylene glycol/polyethylene glycol polymer has a molecular weight of about 1800 Daltons and comprises a compound of the following general formula:

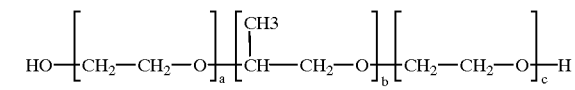

and wherein the surface having the polypropylene glycol/polyethylene glycol polymer covalently attached thereto defines a surface contact angle less than about 45 degrees and exhibits an insulin adsorption profile of less than about 1.0 microgram per square centimeter.

2. The medical device of claim 1 wherein the surface contact angle is less than about 35 degrees.

3. The medical device of claim 1 wherein the surface exhibits an insulin adsorption profile of less than about 0.5 microgram per square centimeter.

4. The medical device of claim 1 wherein the surface exhibits an insulin adsorption profile of less than about 0.1 microgram per square centimeter.

5. The medical device of claim 1, wherein the surface is metallic.

6. The medical device of claim 5, wherein the surface is titanium.

7. The medical device of claim 1, wherein the surface is non-metallic.

8. The medical device of claim 1, wherein the medical device is selected from the group consisting of a prefilled medication cartridge, a syringe and a catheter.

9. The medical device of claim 1 wherein the medical device is externally worn.

10. The medical device of claim 1 wherein the medical device is implantable.

11. A method of inhibiting the denaturation of insulin on a surface comprising covalently attaching to the surface a polypropylene glycol/polyethylene glycol polymer comprising the following general formula:

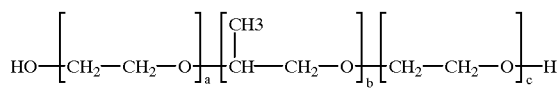

wherein the polypropylene glycol/polyethylene glycol polymer has a molecular weight of about 1800, and wherein the treatment produces a surface that defines a surface contact angle less than about 45 degrees and exhibits an insulin adsorption profile of less than about 1.0 microgram per square centimeter.

12. The method of claim 11, wherein the polypropylene glycol/polyethylene glycol polymer is covalently attached to the surface by a method selected from the group consisting of polymeric attachment, RF-plasma attachment, grafting, or silane-based primer attachment.

13. The method claim 11 wherein the surface contact angle is less than about 35 degrees.

14. The method of claim 11 wherein the surface exhibits an insulin adsorption profile of less than about 0.1 microgram per square centimeter.

15. The method of claim 11 wherein the surface is metallic.

16. The method of claim 15, wherein the surface is titanium.

17. The method of claim 11, wherein the surface is non-metallic.

18. The method of claim 11, wherein the surface is in a medical device.

19. A process for treating a surface to inhibit the denaturation of insulin on the surface comprising covalently attaching to the surface a polypropylene glycol/polyethylene glycol polymer comprising the following general formula:

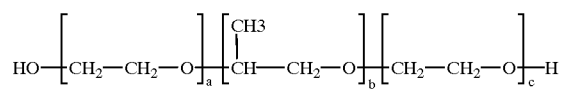

wherein the polypropylene glycol/polyethylene glycol polymer has a molecular weight of about 1800, and wherein the process produces a surface that defines a surface contact angle less than about 45 degrees and exhibits an insulin adsorption profile of less than about 1.0 microgram per square centimeter.

20. A surface produced by the process of claim 19.

* * * * *